Feb. 28, 1961 G. H. MACK Plant Pat. 2,030
CHRYSANTHEMUM PLANT
Filed June 1, 1960
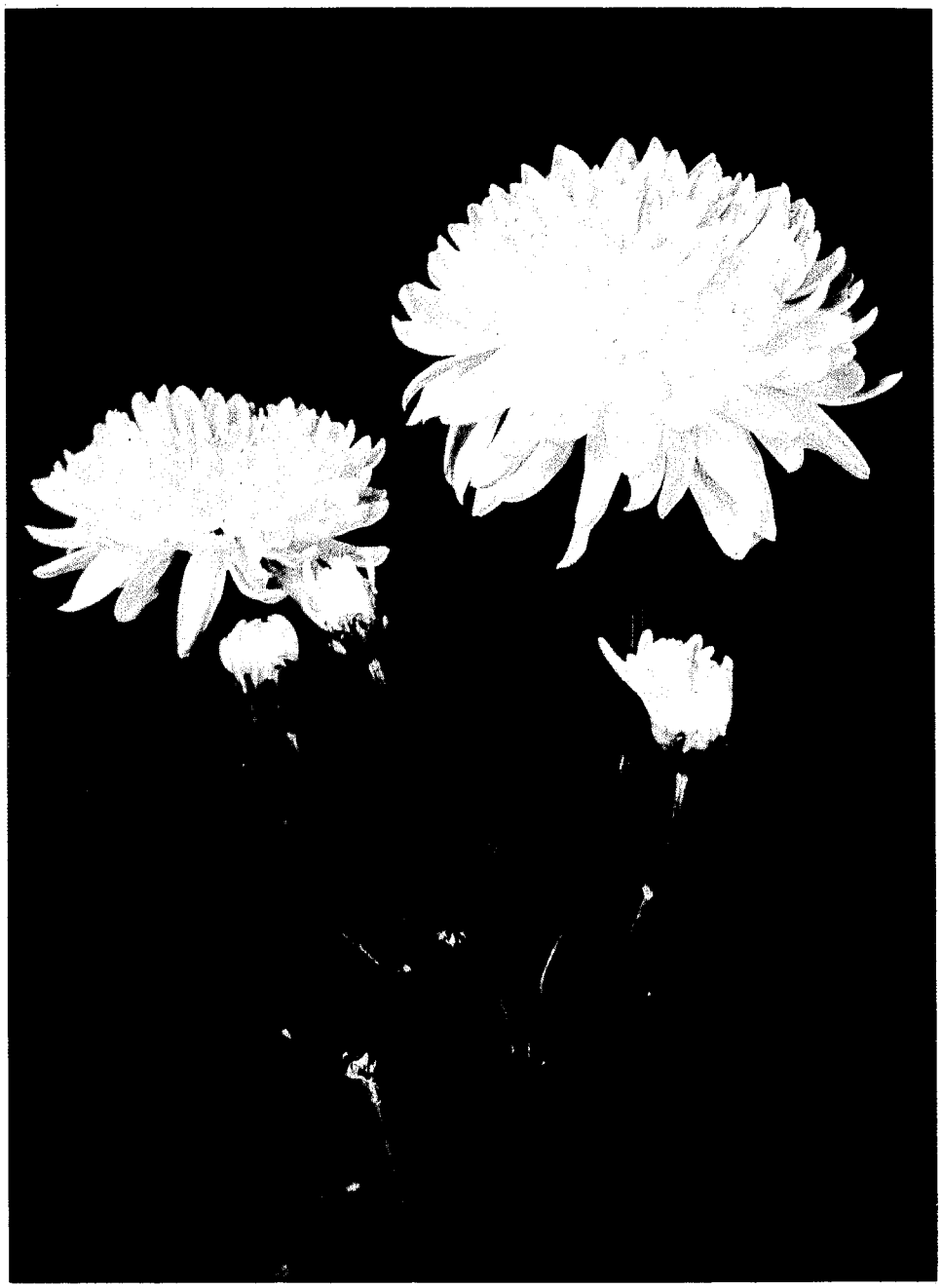
INVENTOR
Grace H. Mack
BY Robb & Robb
ATTORNEYS United States Patent Office Plant Pat. 2,030
Patented Feb. 28, 1961

2,030

CHRYSANTHEMUM PLANT

Grace H. Mack, New Canaan, Conn., assignor to Bristol Nurseries, Inc., Bristol, Conn., a corporation of Connecticut Filed June 1, 1960, Ser. No. 33,352

1 Claim. (Cl. 47—60)

The present invention relates to a new and distinct variety of chrysanthemum plant of the decorative class, which was originated by me by crossing an unnamed and unpatented seedling of "Fascination" (unpatented) with the variety known as "Gardenia" (unpatented).

The primary objective of this breeding was to produce a superior white flowered chrysanthemum variety which is suitable for cut flower use and blooms near mid-season. This objective was fully achieved, along with other desirable improvements, as evidenced by the following unique combination of characteristics which are outstanding in the new variety and which distinguish it from its parents, as well as from all other varieties of which I am aware:

(1) A robustly erect and regal plant habit (the plants being more erect than either parent or the average tall white chrysanthemum varieties);

(2) An early blooming habit (earlier than "Gardenia," "Grace Bradshaw" [unpatented], "Ivory Glow" [unpatented], and other average white chrysanthemums);

(3) A habit of bearing flowers on long, strong stems, with consequent special suitability thereof for cut flowers (the flower stems being stronger than those of most other tall white chrysanthemum varieties); and (4) A distinctive glowing and pure white color tonality of the flowers (purer than other tall whites and seldom showing any pink or yellow tones).

Asexual reproduction of the new variety by softwood top cuttings, as performed by me at New Canaan, Connecticut, shows that these characteristics and distinctions come true to form and are established and transmitted through succeeding propagations.

The accompanying drawing shows typical specimens of the vegetative growth and flowers of my new chrysanthemum variety in various stages of development, and as depicted in color as nearly true as it is reasonably possible to make the same in a color illustration of this character.

The following is a detailed description of the new variety, with color terminology in accordance with general color terms of ordinary dictionary significance, as based upon observations made from specimens grown at both New Canaan and Bristol, Connecticut:

Parentage: An unnamed seedling of "Fascination" × "Gardenia."

Classification: Decorative.

Growth: Tall (about 30 inches); strongly upright (has air of regal erectness); excellent for cutting sprays.

Cold resistance: Above average under proper culture, as determined from comparison with other varieties similarly grown at New Canaan and Bristol, Connecticut, respectively.

Blooming period: In Connecticut, blooms usually commence about October 1 and continue until killing frosts.

*Flower*

Bud:

*Color.*—When sepals first divide—soft pink and cream. When petals begin to unfurl—pale pink and ivory. When half-blown: inside of petals—ivory white; reverse of petals—faintly pink and cream.

*Peduncle.*—Color—dark green, but often purple-ebony. Strength—outstandingly firm.

Bloom:

*Size.*—3 inches.

*Stem.*—Sturdy; straight.

*Form.*—Decorative.

*Petalage.*—Long; strap-like.

*Color.*—Center of flower—pale ivory cream. Outer petals—pure alabaster white. Base of petals—deep ivory. Inside of petals—pure alabaster white. Reverse of petals—pure white, but becoming pale pink after hard frost.

General color tonality.—Glowing pure white of waterlily effect.

*Petals.*—Texture—leathery; firm. Form—Strap-like; occasionally incurved slightly; translucent.

*Fragrance.*—Average chrysanthemum fragrance but not outstanding.

*Plant*

Form: Rather wedge-like (comparable to an inverted pyramid).

Growth: Tall; erect; long-stemmed; bushy tops.

Foliage:

*Size.*—Length—3 inches. Width—1½ inches.

*Quantity.*—Average.

*Color.*—Upper side—deep, waxey green. Reverse side—paler green (medium depth).

*Texture.*—Firm; crisp; sharply pointed.

I claim:

A new and distinct variety of chrysanthemum plant of the decorative class, substantially as herein shown and described, characterized particularly as to novelty by the unique combination of a robustly erect and regal plant habit, an early blooming habit averaging about mid-season, a habit of bearing flowers on long and strong stems, with consequent special suitability thereof for cut flowers, and a distinctive glowing and pure white general color tonality of the flowers.

No references cited.